(12) United States Patent
Feingold

(10) Patent No.: US 9,017,401 B2
(45) Date of Patent: Apr. 28, 2015

(54) LENS INSERTER APPARATUS AND METHOD

(71) Applicant: Vladimir Feingold, Laguna Niguel, CA (US)

(72) Inventor: Vladimir Feingold, Laguna Niguel, CA (US)

(73) Assignee: Presbitech, Inc., Los Angeles, CA (US)

( * ) Notice: Subject to any disclaimer, the term of this patent is extended or adjusted under 35 U.S.C. 154(b) by 123 days.

(21) Appl. No.: 13/908,557

(22) Filed: Jun. 3, 2013

(65) Prior Publication Data

US 2013/0317513 A1 Nov. 28, 2013

Related U.S. Application Data

(62) Division of application No. 12/704,162, filed on Feb. 11, 2010, now Pat. No. 8,454,687.

(51) Int. Cl.
*A61F 2/16* (2006.01)
*A61F 9/013* (2006.01)
*A61F 2/14* (2006.01)

(52) U.S. Cl.
CPC ................. *A61F 9/013* (2013.01); *A61F 2/146* (2013.01)

(58) Field of Classification Search
None
See application file for complete search history.

(56) References Cited

U.S. PATENT DOCUMENTS

| | | | |
|---|---|---|---|
| 4,681,102 A | 7/1987 | Bartell | |
| 4,919,130 A | 4/1990 | Stoy et al. | |
| 4,934,363 A | 6/1990 | Smith et al. | |
| 5,066,297 A | 11/1991 | Cumming | |
| 5,098,439 A | 3/1992 | Hill et al. | |
| 5,123,905 A | 6/1992 | Kelman | |
| 5,582,614 A | 12/1996 | Feingold | |
| 5,643,276 A | 7/1997 | Zaleski | |
| 6,050,999 A | 4/2000 | Paraschac et al. | |
| 6,056,757 A | 5/2000 | Feingold et al. | |
| 6,554,839 B2 | 4/2003 | Brady | |
| 6,581,993 B2 | 6/2003 | Nigam | |
| 7,097,649 B2 | 8/2006 | Meyer | |
| 8,162,953 B2 | 4/2012 | Dishler et al. | |
| 8,246,631 B2 | 8/2012 | Pynson | |
| 2004/0059343 A1 | 3/2004 | Shearer et al. | |
| 2004/0117012 A1 | 6/2004 | Vincent | |
| 2005/0283163 A1 | 12/2005 | Portney et al. | |
| 2006/0004381 A1 | 1/2006 | Feingold et al. | |
| 2006/0235430 A1 | 10/2006 | Le et al. | |
| 2008/0275462 A1 | 11/2008 | Feingold et al. | |

FOREIGN PATENT DOCUMENTS

| | | |
|---|---|---|
| JP | 2006522674 A | 10/2006 |
| JP | 2008513044 A | 5/2008 |
| JP | 2009028223 A | 2/2009 |

OTHER PUBLICATIONS

Office Action for corresponding Japanese Application No. 2012-552858, dated Nov. 18, 2013.
Office Action for corresponding Chinese Application No. 201080066124.X, dated Jan. 28, 2014.

*Primary Examiner* — Thomas McEvoy
(74) *Attorney, Agent, or Firm* — Victor Siber, Esq.; Andres Arrubla, Esq.

(57) ABSTRACT

A method for inserting a lens into a corneal pocket or flap includes providing a lens inserter device, opening a first leaf and a second leaf of the device, positioning a slot of each one of a first and a second lens shaped portion over a post on a packaging of the lens, positioning the lens between the first leaf and the second leaf, inserting the lens into the corneal pocket, and releasing the lens from the lens inserter device.

5 Claims, 6 Drawing Sheets

LENS INSERTER APPARATUS AND METHOD

RELATED APPLICATIONS

This application is a divisional of U.S. patent application Ser. No. 12/704,162, entitled Lens Inserter Apparatus and Method, filed Feb. 11, 2010.

FIELD OF THE INVENTION

The present invention relates generally to ocular surgery. More particularly, the present invention relates to a method for inserting a lens into the eye to treat presbyopia.

BACKGROUND OF THE INVENTION

Presbyopia is the gradual loss of near vision, which often accompanies the aging process. The eyes of a person suffering from presbyopia have a diminished ability to focus on near objects such as books, magazines, or a computer screen. Symptoms of presbyopia can include difficulty reading fine print and blurred vision when transitioning the focus of the eye between near and distant objects.

There are several common treatments for presbyopia. A dedicated pair of reading glasses is one such treatment. Reading glasses provide magnification of near objects to provide for improved vision. However, if a person also needs glasses to focus on distant objects switching between reading glasses and distance glasses can be inconvenient. Another treatment is bifocal glasses, which provide a portion of the glasses lens for assisting with distance vision and a portion for assisting with near vision. While bifocals provide a single pair of glasses for both near and distance vision correction, they can cause disorientation. Contact lenses for the surface of the eye have also been developed which provide vision correction for both near and distance vision. Although these treatments provide vision correction for a person suffering from presbyopia, each requires at least one an additional accessory or pair of contact lenses that must be worn or used daily. Additionally, very small lenses for insertion into the eye are being developed. However, these lenses cannot be handled manually or with conventional tools.

Accordingly, it is desirable to provide an apparatus and method for inserting a lens into the cornea to improve a patient's presbyopia.

SUMMARY OF THE INVENTION

The foregoing needs are met, to a great extent, by the present invention, wherein in one aspect an apparatus is provided that in some embodiments includes a design for a lens inserter apparatus and method.

In accordance with one aspect of the present invention, a lens inserter apparatus includes a handle having a distal end and a proximal end and an outer wall of the handle defining a lumen extending through the handle and a plunger extending movably through the lumen of the handle having a distal end and a proximal end, wherein the plunger includes a distal segment which extends beyond the distal end of the handle. The lens inserter can also include an actuator coupled to the plunger configured to provide movement to the plunger. Additionally, the lens inserter can include a leaf extending from the distal end of the handle and configured to hold the lens to be inserted into the eye, wherein the leaf defines a slot configured to enable loading the lens onto the inserter.

In accordance with another aspect of the present invention the lens inserter apparatus can include two leaves. The first leaf can extend from a top surface of the distal end of the handle and the second leaf can extend from a bottom surface of the distal end of the handle. The leaves can be configured to grip the lens to be inserted into the eye. Additionally, the lens inserter can include a spring disposed within the lumen of the handle against which the plunger is biased.

In accordance with another aspect of the present invention, the actuator of the lens inserter can provide movement to the plunger about a radial axis of the plunger. In addition, the actuator can provide movement to the plunger about a longitudinal axis of the plunger. Alternately, the actuator of the lens inserter can provide movement to the plunger about a radial axis of the plunger and a longitudinal axis of the plunger.

In accordance with another aspect of the present invention, the slot of the lens inserter can be configured to couple with a post on a package holding the lens. The distal end of the distal segment of the plunger can include a fork configured to push the lens off of the leaf. Additionally, the actuator can include a finger rest, and the leaf can include a lens shaped portion to pick up and hold the lens for insertion.

In accordance with yet another aspect of the present invention, an apparatus for inserting a lens into a corneal pocket or flap includes a handle having an outer wall defining a lumen extending through the handle. The lens inserter can include a plunger extending movably through the lumen of the handle, wherein the plunger includes a distal segment, which extends beyond the distal end of the handle. The lens inserter can include an actuator coupled to the plunger and extending through an opening defined by the outer wall of the handle wherein the actuator is configured to provide movement to the plunger about a radial and longitudinal axis of the plunger. The lens inserter can also include a pair of leaves extending from the distal end of the handle and configured to grip the lens to be inserted into the eye. The leaves can define a slot configured to enable loading the lens onto the inserter, and the leaves can be biased together and can be separated by using the actuator to provide radial movement to the plunger.

In accordance with another aspect of the present invention the actuator can include a finger rest. The slot at the distal end of the leaf can be configured to couple with a post on a package holding the lens. Additionally, the distal end of the distal segment plunger can include a fork configured to push the lens off of the leaf.

In accordance with still another aspect of the present invention, a method for inserting a lens into a corneal pocket or flap includes opening a set of leaves of a device for inserting the lens into the pocket in the cornea; and positioning a slot at a distal end of one of the leaves over a post on a packaging of the lens. The method further includes positioning the lens between the leaves of the device for inserting the lens. Additionally, the method includes inserting the lens into the corneal pocket and releasing the lens from the leaves.

In accordance with even another aspect of the present invention, the method can further include releasing the lens from the leaves by moving the actuator along a longitudinal axis of the plunger to move the plunger in a direction of a distal end of the device to insert the lens. The method can also include the leaves being biased together. The method can also include the device for inserting the lens including a spring for biasing against the plunger. The method can include using an actuator to rotate a plunger of the device about a radial axis of the plunger to open the leaves, and using the actuator to close the leaves in order to grip the lens between the two leaves.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
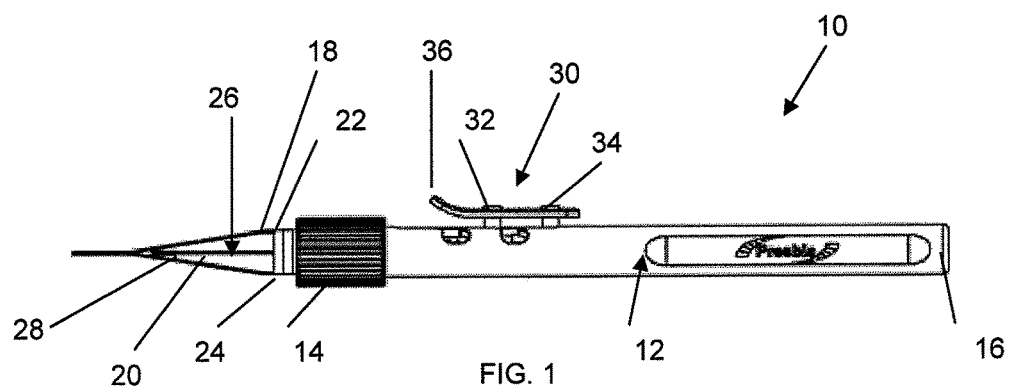
FIG. 1 illustrates a side view of a lens inserter apparatus in accordance with an embodiment of the invention.

The invention will now be described with reference to the drawing figures, in which like reference numerals refer to like parts throughout. An embodiment in accordance with the present invention provides an apparatus and method for inserting a lens into a flap or pocket in the cornea. This lens or pocket preferably is created by a laser used in conventional lasik surgery. The apparatus includes a handle, a plunger extending movably through the lumen of the handle, wherein the plunger includes a distal segment that extends beyond the distal end of the handle, an actuator coupled to the plunger configured to provide movement to the plunger, and a leaf extending from the distal end of the handle and configured to hold the lens to be inserted into the eye, wherein the leaf defines a slot configured to enable loading the lens onto the inserter.

An embodiment of the present inventive apparatus is illustrated in FIG. 1. FIG. 1 illustrates a side view of a lens inserter apparatus 10 in accordance with an embodiment of the invention. The lens inserter apparatus 10 includes a handle 12, which has a distal end 14 and a proximal end 16. The lens inserter 10 also includes a pair of leaves 18 and 20, which extend from the distal end 14 of the handle 12. Preferably, the leaves 18 and 20 have a length in a range of 10 mm to 30 mm and a width in a range of 1 mm to 4 mm. The thickness of each of leaves 18 and 20 is approximately in the range of 50 microns to 200 microns for a combined thickness in a range of 100 microns to 400 microns. The leaves can be formed from stainless steel or any other suitable non corrosive material. Top leaf 18 extends from a top surface 22 of the handle 12, while bottom leaf 20 extends from a bottom surface of the handle 12. The top leaf 18 and bottom leaf 20 are biased together, such that an inner surface of the top leaf 18 is in contact with an inner surface of the bottom leaf 20, and are preferably made from a flexible, resilient material. Additionally, a plunger 26 extends through the handle 12. The plunger 26 has a distal end portion 28, which extends beyond the distal end 14 of the handle 12. The plunger can be formed from titanium or stainless steel or any other suitable non corrosive material. An actuator 30 is coupled to the plunger 26 by posts 32 and 34. The actuator 30 can be used to move the plunger 28 via finger rest 36. The lens inserter apparatus 10 also includes a longitudinal axis "a."

Figure 2:
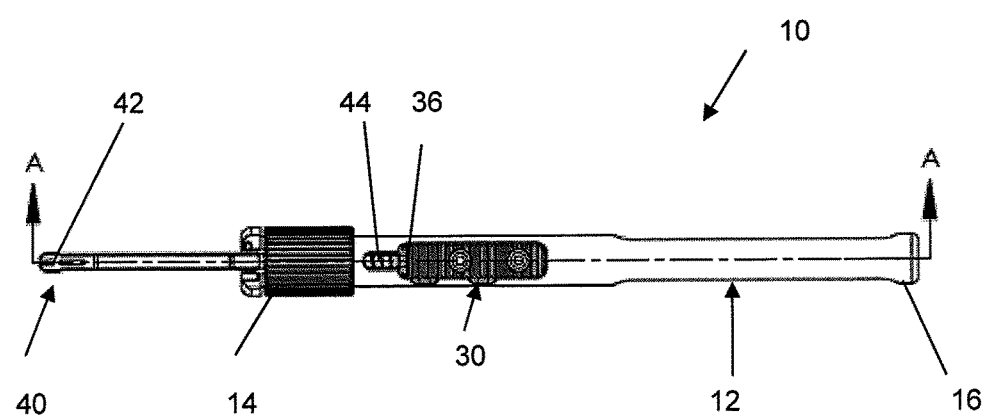
FIG. 2 illustrates a top view of a lens inserter in accordance with an embodiment of the invention.

FIG. 2 illustrates a top view of a lens inserter in accordance with an embodiment of the invention. The leaves 18 and 20 have a generally flat elongate surface 38 and a distal end 40, which has a generally circular, lens shaped portion 42, which allows for the lens to be inserted into the eye to sit on a top surface of the bottom leaf 20. The generally circular lens shaped portion preferably has a diameter in a range of 2 mm to 4 mm. As illustrated in FIG. 2, the outer wall of the handle 12 also defines a slot 44 in which the actuator 30 can move in order to provide movement to the plunger 26. The finger rest 36 of the actuator 30 can also be textured to provide friction between the actuator and the operator's finger.

Figure 3:
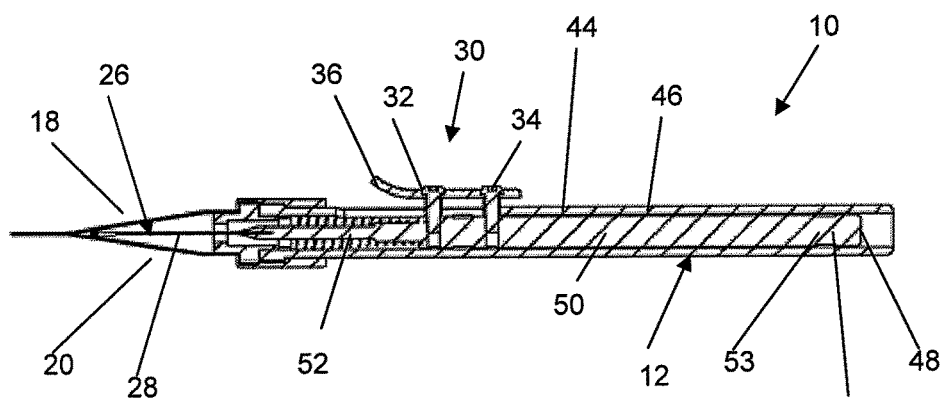
FIG. 3 illustrates a sectional view taken along axis "A" of the embodiment shown in FIG. 2.

FIG. 3 illustrates a sectional view taken along axis "a" of the embodiment shown in FIG. 1. The outer wall 46 of the handle 12 defines a lumen 48, which extends through the length of the handle 12. The plunger 26 is positioned within the lumen 48 of the handle 12. The plunger 26 includes a body portion 50 having a longitudinal and radial axis and is coupled to the actuator 30 via posts 32 and 34. The body 50 of the plunger 26 is movably disposed within the lumen 48 of the handle and can be moved along both the longitudinal and radial axis of the plunger 26. The plunger 26 can also be biased against a spring 52 disposed about a distal end 54 of the plunger 26 within the lumen 48 of the handle 12. The plunger 26 also includes the distal segment 28, which extends beyond the distal end 54 of the plunger 26 and the distal end 14 of the handle 12. The distal segment 28 of the plunger 26 is positioned between the leaves 18 and 20 of the lens inserter 10. The distal segment 28 of the plunger 26 preferably has a thickness in a range of 100 microns to 300 microns. The plunger 26 can also include a ring 53 at the proximal end 54 of the body portion 50 of the plunger 26. The ring 53 preferably can be formed of a material, which slides easily within the lumen 48 of the handle 12.

Figure 4:
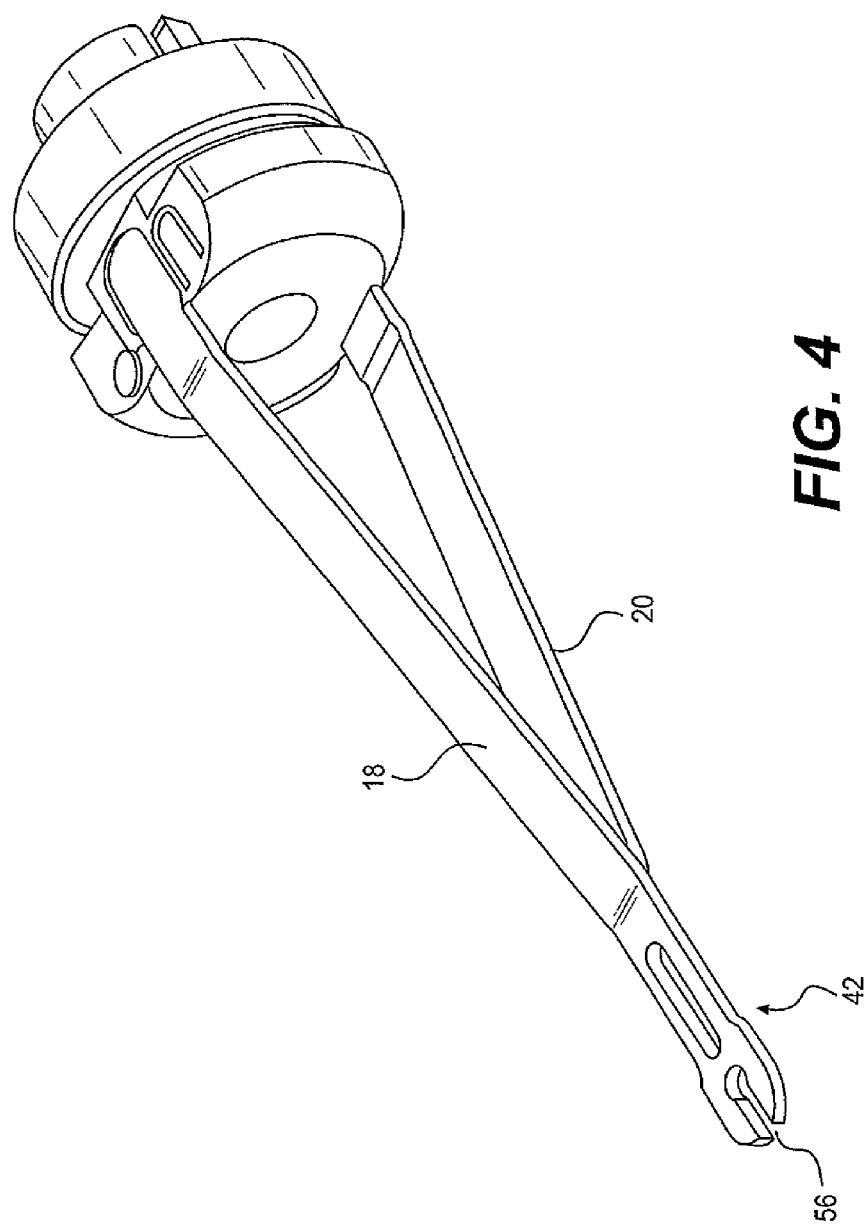
FIG. 4 illustrates a perspective view of a distal end of the lens inserter apparatus in accordance with an embodiment of the invention.
Figure 5:
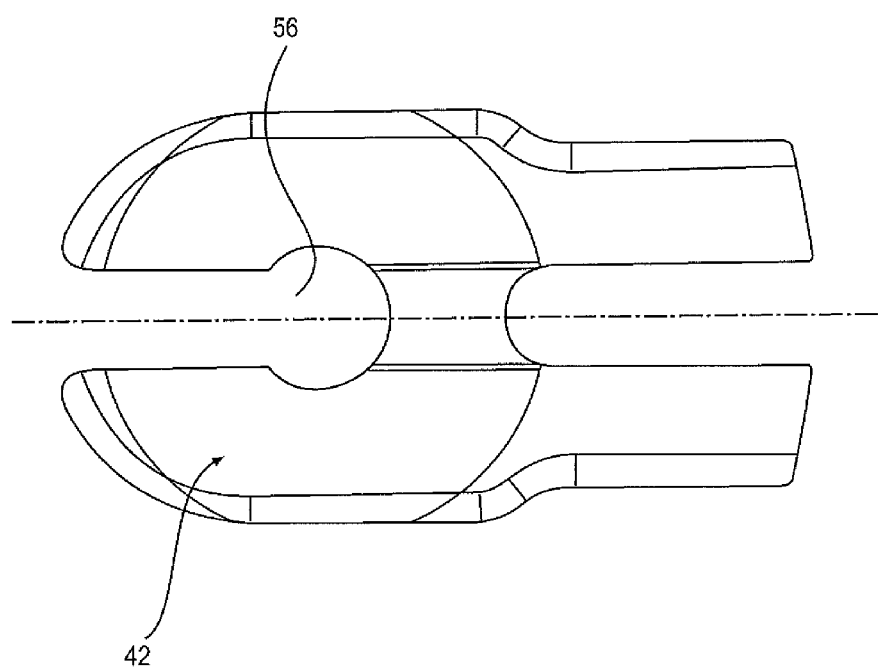
FIG. 5 illustrates a top view of the distal end of the lens inserter apparatus shown in FIG. 4.

FIG. 4 illustrates a perspective view of a distal end of the lens inserter apparatus 10 in accordance with an embodiment of the invention, and FIG. 5 illustrates a top view of the distal end of the lens inserter apparatus 10 shown in FIG. 4. FIGS. 4 and 5 show the distal end 40 of the leaves 18 and 20. The distal end 40 of each of the leaves 18 and 20 includes a generally flat lens shaped portion 42. The lens shaped portion 42 is configured to allow a lens designed be inserted into a flap or pocket in the cornea of the eye to sit on top of the surface of the distal end 40 of the bottom leaf 20. The distal end 40 of the leaves 18 and 20 also includes a slot 56. The slot 56 can be configured to enable loading the lens onto the inserter 10. Additionally, the inner surfaces of the distal end 40 of the leaves 18 and 20 sit on top of one another in order to grip the lens for insertion into the pocket or flap in the cornea.

Figure 6:
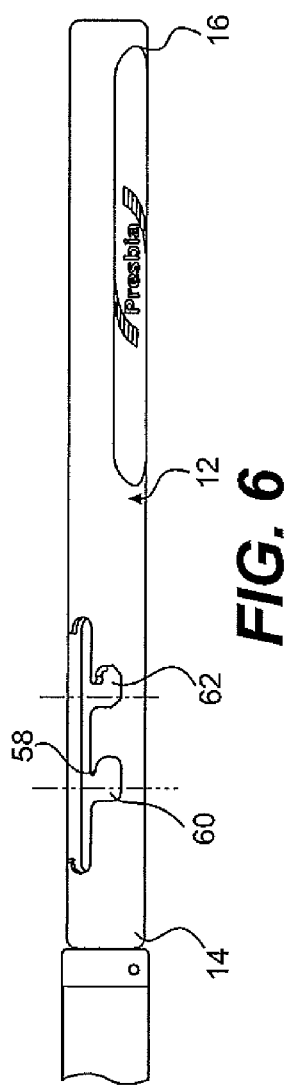
FIG. 6 illustrates a side view of a handle of a lens inserter in accordance with an embodiment of the invention.

FIG. 6 illustrates the handle 12 of the lens inserter 10 in further detail. The handle 12 includes an outer wall 46 that defines an opening 58. The actuator 30, not shown, can extend through the opening 58 and move within the opening 58. The opening can be shaped such that the actuator 30 can be moved along the longitudinal axis of the plunger 26 or the radial axis of the plunger 26. The opening 58 includes notches 60 and 62 such that the actuator 30 can be moved along the radial axis of the plunger 26.

Figure 7:
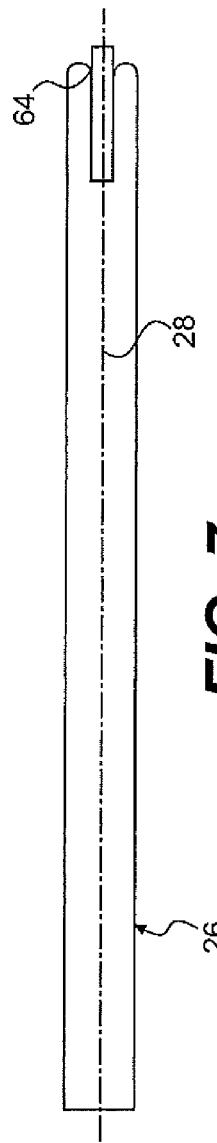
FIG. 7 illustrates a top view of a plunger of a lens inserter in accordance with an embodiment of the invention.
Figure 8:
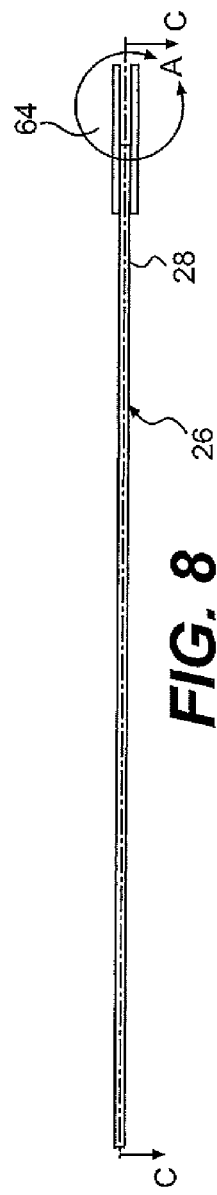
FIG. 8 illustrates a side view of a plunger of a lens inserter in accordance with an embodiment of the invention.

FIG. 7 illustrates a top view of a plunger 26 of a lens inserter 10 in accordance with an embodiment of the invention, and FIG. 8 illustrates a side view of a plunger 26 of a lens inserter 10 in accordance with an embodiment of the invention. FIGS. 7 and 8 illustrate the distal segment 28 of the plunger 26. The distal segment 28 is generally flat and includes a fork 64 at the distal end 66 of the distal segment 28 configured to push the lens off of the lens shaped portion 42 of the leaves 18 and 20.

Figure 9:
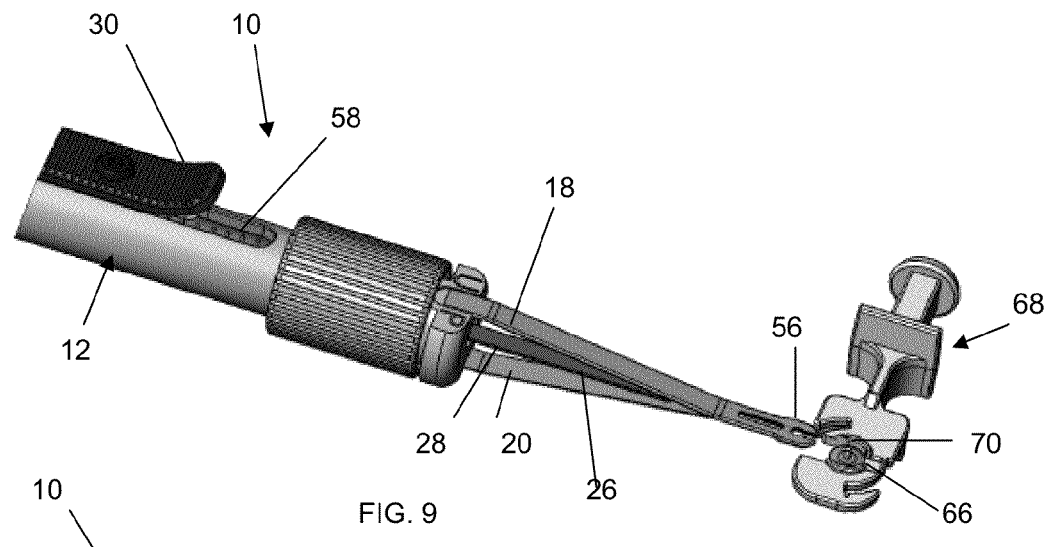
FIG. 9 illustrates a step in a method of inserting a lens using a lens inserter apparatus in accordance with an embodiment of the invention.
Figure 10:
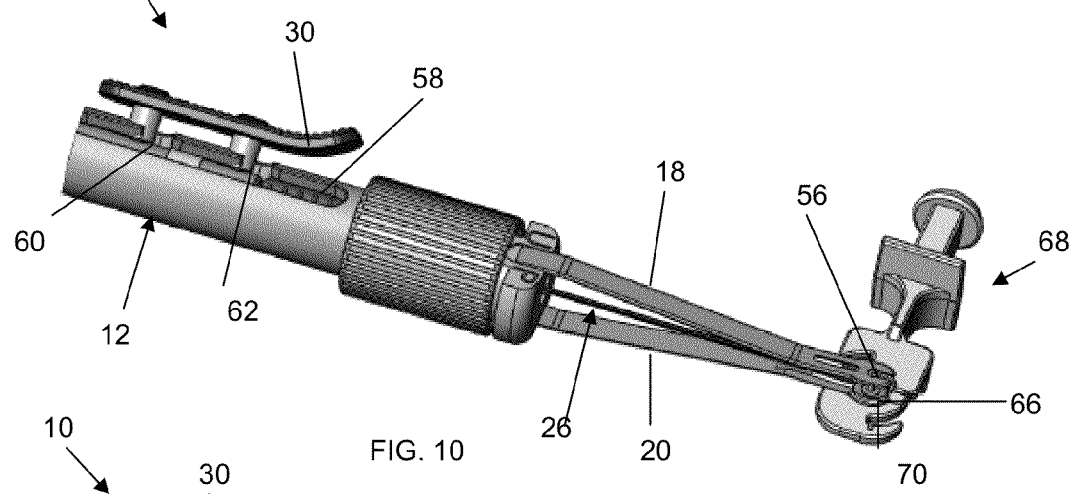
FIG. 10 illustrates a step in a method of inserting a lens using a lens inserter apparatus in accordance with an embodiment of the invention.
Figure 11:
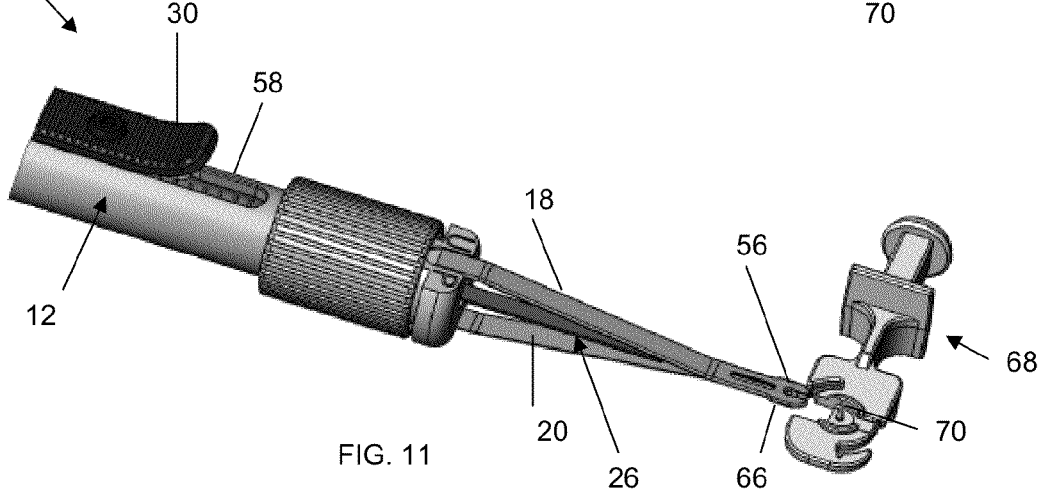
FIG. 11 illustrates a step in a method of inserting a lens using a lens inserter apparatus in accordance with an embodiment of the invention.

FIGS. 9-11 illustrate a method of inserting a lens into a pocket or flap in a cornea in accordance with an embodiment of the invention. FIG. 9 illustrates the lens inserter 10 and a lens 66 for placement in the pocket or flap in the cornea. However, it is important to note that the lens inserter 10 can be used with any lens and packaging for the lens. Preferably, the lens 66 is approximately 2.5 mm to 3.5 mm in diameter and has an edge thickness of less than 20 microns. Although any lens suitable for insertion into a pocket or flap in a cornea can be used. As shown in FIGS. 9-11, the lens 66 is disposed in packaging 68. Packaging 68 includes a post 70. As shown in FIG. 10, the actuator 30 can be rotated about the radial axis of the plunger 26 into notches 60 and 62 of the handle 12, in order to open the leaves 18 and 20. As the plunger 26 is rotated it spreads the leaves 18 and 20 enough to place the bottom leaf 20 under the lens 66. The slot 56 at the distal end 40 of the leaves 18 and 20 can slide around the post 70 of the packaging to enable grasping of the lens 66. When the lens 66 is positioned on the lens shaped portion 42 of the bottom leaf 20, the actuator 30 can be rotated back out of the notches 60 and 62 in order to close the leaves and grasp the lens.

Figure 12:
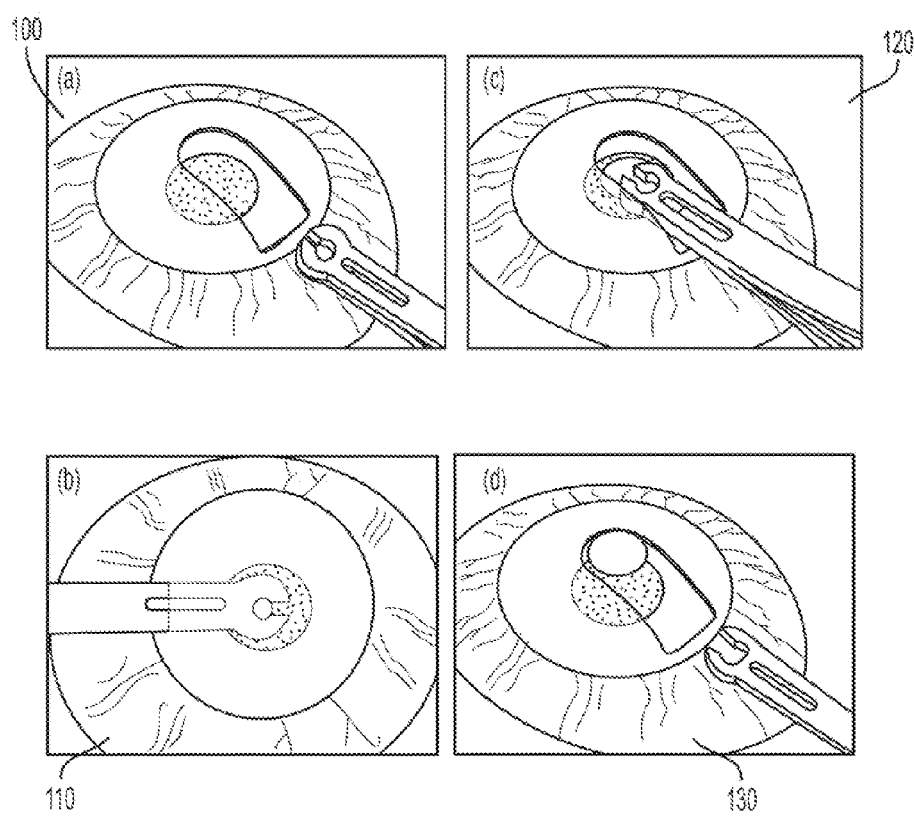
FIG. 12 illustrates a step in a method of inserting a lens using a lens inserter apparatus in accordance with an embodiment of the invention.

FIG. 12 illustrates a method of inserting a lens into a pocket or flap in a cornea in accordance with an embodiment of the invention. Step 100 shows the distal end 40 of the leaves 18 and 20 grasping the lens 66, and a pocket 72 in the cornea 74 of the eye 76. Step 110 shows the lens inserter 10 inserted into the pocket 72. Step 120 shows the plunger 26 being advanced to push the lens 66 off of the leaves 18 and 20. Additionally, step 130 shows the lens 66 placed in the eye 76 and the lens inserter 10 being removed from the eye 76.

The many features and advantages of the invention are apparent from the detailed specification, and thus, it is intended by the appended claims to cover all such features and advantages of the invention, which fall within the true spirit, and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for inserting a lens into a corneal pocket or flap comprising:
   providing a lens inserter device that comprises:
      a handle having a distal end and a proximal end and an outer wall of the handle defining a lumen extending through the handle;
      a plunger extending movably through the lumen of the handle having a distal end and a proximal end, wherein the plunger includes a distal segment, which extends beyond the distal end of the handle;
      an actuator coupled to the plunger configured to provide movement to the plunger;
      a first leaf extending from a top surface of the distal end of the handle and having a circular lens shaped portion at a free end which defines a circumferential center; and
      a second leaf extending from a bottom surface of the distal end of the handle and having a second circular lens shaped portion at a free end which defines a circumferential center;
   wherein the first leaf and the second leaf are biased to engage each other and configured to hold the lens to be inserted into the eye between the first and second circular lens shaped portions,
   wherein the plunger is configured to separate an engaged first leaf and second leaf upon a rotational movement of the actuator, and
   wherein each of the first and second lens shaped portions define a slot, each slot extending through an entire thickness of the respective first and second circular lens shaped portion while extending from the respective free end to each center of the first and second circular lens shaped portions;
   opening the first leaf and the second leaf of the device;
   positioning the slot of each one of the first and second lens shaped portions over a post on a packaging of the lens;
   positioning the lens between the first leaf and the second leaf;
   inserting the lens into the corneal pocket; and
   releasing the lens from the lens inserter device.

2. The method of claim 1 further comprising releasing the lens from the lens inserter device by moving the actuator along a longitudinal axis of the plunger to move the plunger in a direction of a distal end of the device to insert the lens.

3. The method of claim 1 further comprising, wherein the lens inserter device further comprises a spring for biasing against the plunger.

4. The method of claim 1 further comprising using the actuator to rotate the plunger of the device about a radial axis of the plunger to open the first leaf and the second leaf.

5. The method of claim 1 further comprising using the actuator to close the first leaf and the second leaf in order to grip the lens between the first leaf and the second leaf.

* * * * *